United States Patent [19]

Shen

[11] 4,387,709

[45] Jun. 14, 1983

[54] KNEE BRACE

[76] Inventor: C. Anthony Shen, 13800 Arizona St., Suite 101, Westminster, Calif. 92683

[21] Appl. No.: 282,432

[22] Filed: Jul. 13, 1981

[51] Int. Cl.³ .............................................. A61F 5/04
[52] U.S. Cl. ............................... 128/87 R; 128/89 R; 128/80 C
[58] Field of Search ..................... 128/80 C, 80 R, 83, 128/87 R, 89 R, 90, 165; 2/22, 24

[56] References Cited

U.S. PATENT DOCUMENTS

| 365,612 | 6/1887 | Lee | 128/89 R |
| 3,853,123 | 12/1974 | Moore | 128/80 C |
| 3,955,565 | 5/1976 | Johnson, Jr. | 128/89 R |
| 4,041,940 | 8/1977 | Frankel et al. | 128/80 C |

FOREIGN PATENT DOCUMENTS 237698  5/1945  Switzerland ...................... 128/80 B Primary Examiner—John D. Yasko Attorney, Agent, or Firm—Knobbe, Martens, Olson, Hubbard & Bear

[57] ABSTRACT

A device for immobilizing the knee of an individual is an open-ended, tubular shell formed of an integral piece of semi-rigid material having portions shaped to receive the lower thigh, knee, and upper calf of the individual. The device is easily slipped on and off by means of expansion of a longitudinal opening which bifurcates one side of the device. After the device is placed around the individual's leg, the opening can be closed to tighten the shell around the leg forming the shell into an essentially closed open-ended tube which has substantial structural strength to provide secure immobilization. The thigh and calf portions of the device have flat areas to prevent rotation of the individual's leg within the device. The thigh portion extends at an angle from the calf portion sufficient to immobilize the individual's knee in a flexed position in which the ligaments are relaxed.

6 Claims, 7 Drawing Figures

KNEE BRACE

BACKGROUND OF THE INVENTION

The invention is generally related to devices for immobilizing an individual's knee and specifically, to those devices which can be easily slipped on and off the individual.

Permanent casts, made of plaster, polyethylene and various types of braces and splints, are well known for immobilizing an individual's knee that has suffered an injury, such as a fracture, sprain, ligament damage, or the like. Such permanent casts are not designed to be removed and reused. Braces, such as those made of elastomeric fabric, while readily removable, do not provide optimum immobilization.

Recently, efforts have been made to produce a device which can be easily slipped on and off the individual and yet provide proper immobilization. One such device consists of a first curved piece of polyethylene which, when in position, is large enough to cover the back and sides of an individual's thigh, knee, and calf. A second, smaller curved piece of polyethylene is large enough to span the open side of the first piece covering the front of the individual's leg. Each of the polyethylene portions is laminated to an inner foam liner. The device is secured to the patient's leg by buckling laterally spaced straps which are anchored to opposing sides of the first piece and extend across the second piece.

While this device solves some of the problems of past devices, it has several disadvantages. Some of these disadvantages are that the device does not adequately prevent rotation of an individual's leg therein, that the dual pieces do not provide sufficient strength and rigidity for proper immobilization, and the knee is not held at a sufficient angle to provide for optimum relaxation of the knee ligaments upon immobilization. Moreover, the padding of the device prevents it from controlling rotation of the individual's knee and from being easily modified for a custom fit.

SUMMARY OF THE INVENTION

The present invention obviates the above-described disadvantages of prior devices. The novel device is particularly adapted for temporary immobilization of knee injuries, such as fractures, sprains, ligament damage, and other soft tissue trauma of the knee.

The inventive device is a unitary, open-ended hollow body of semi-rigid material having thigh, knee, and calf portions shaped to receive the lower thigh, knee, and upper calf, respectively, of the individual. A longitudinal opening bifurcates one side of the body. The size of the opening is adjusted with locking straps to permit the device to be easily slipped on and off.

Thus, once the body is placed around the individual's thigh, knee, and calf, the longitudinal opening can be closed by tightening the locking straps, thereby tightening the body contiguously around the individual's leg forming the body into an essentially closed open-ended tube having substantial structural strength to provide secure immobilization.

The thigh and calf portions of the device have flat areas to prevent rotation of an individual's leg within the device. The thigh portion extends at an angle from the calf portion so that the knee is held in a fixed position, i.e., the ligaments are relaxed, which is important for proper immobilization of the knee.

The device is easily and inexpensively manufactured due to the unitary molded body which has no padding lining its interior. Lack of padding allows the device to more securely immobilize the patient's knee and also allows the device to be easily custom fit by trimming it with a cutting implement.

BRIEF DESCRIPTION OF THE DRAWINGS

These and other advantages will be amplified in the following discussion which makes reference to the accompanying drawings in which.

DETAILED DESCRIPTION OF THE PREFERRED EMBODIMENT

Figure 1:
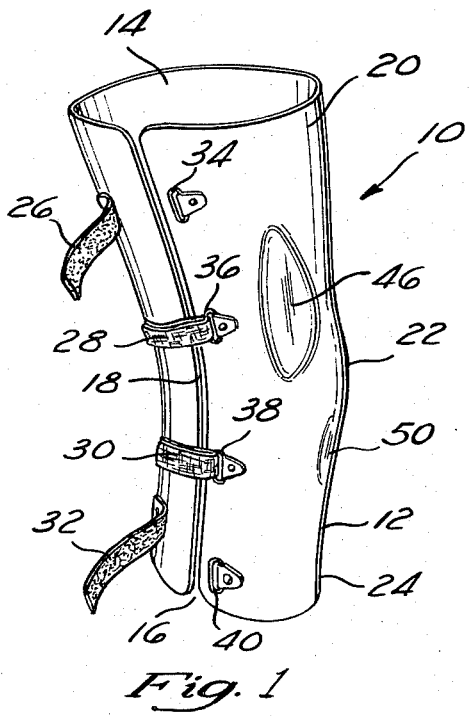
FIG. 1 is a perspective view of the knee brace device depicting the longitudinal opening and locking straps.
Figure 2:
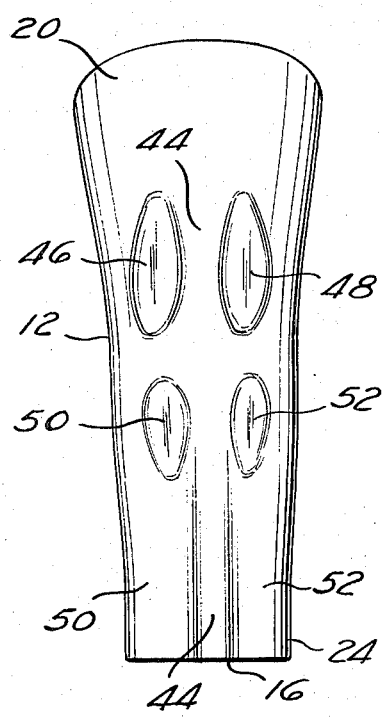
FIG. 2 is a front view of the knee brace.

Referring to FIGS. 1 and 2, a device 10 is shown formed by a tubular shell 12 having an open end 14 for the patient's thigh and an open end 16 for the patient's calf. A narrow longitudinal opening 18 bifurcates a right side of the shell 12 and extends the length of the device 10.

The shell 12 is formed of a semi-rigid material which is sufficiently rigid to immobilize a patient's lower thigh, knee, and upper calf, but is sufficiently pliable to permit the device to be easily slipped on and off the patient as will be hereinafter described. A material found satisfactory is polyethylene. Such a material is also unaffected by moisture which permits the patient to undergo hydro-therapy without removal of the device.

Although the device 10 is an integral unit, it can be conceptualized as having thigh, knee, and calf portions 20, 22, 24 which are shaped to cover the thigh, knee, and calf, respectively, of the patient.

Unlike some prior devices, the interior of the shell 12 is not lined with a cushioned material. This lack of padding allows the shell 12 to fit contiguously and snugly against the patient's skin providing for more secure immobilization. Moreover, the device 10 can be readily custom-fit for a particular patient by trimming the shell 12 with a cutting implement. Specifically, the length of the thigh and calf portions 20,24 can be cut to the length required by the individual with ordinary scissors. Moreover, if any harmful pressure points develop due to a particular bone prominence of the individual, a cast saw can be used to cut into the shell 12 to relieve the pressure.

Referring to FIG. 1, four straps 26, 28, 30, 32 are longitudinally spaced along the length of the shell 12 and are secured to one side of the opening 18 by any suitable means, such as rivets. The upper sides of the straps 26, 28, 30, 32 have a first portion which is fibrous and a second portion which is roughened. An example of a suitable material is that sold under the trademark Velcro ®. Buckles 34, 36, 38, 40 are riveted to the opposite side of the opening 18 in opposing relation to straps 26, 28, 30, 32, respectively. Each of the straps 26, 28, 30, 32 can be threaded through its opposing buckle 34, 36, 38, 40 and doubled over itself so that the roughened portion contacts the fibrous portion to effect a lock. As shown in FIG. 1, straps 28 and 30 are in the locked configuration. It should be understood that although Velcro ® has been found most satisfactory, other locking mechanisms could be used.

Figure 3:
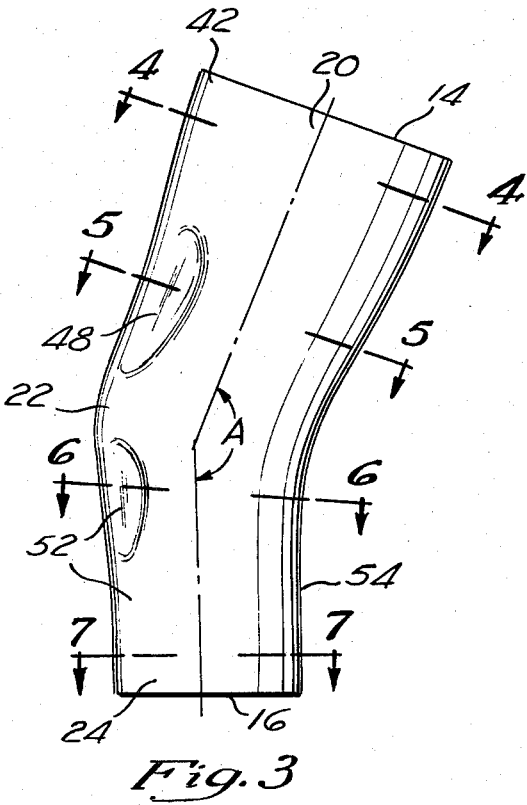
FIG. 3 is a side view of the knee brace showing the angle formed between the thigh and calf portions.

As best shown in FIG. 3, the knee portion 22 is curved to provide an angle A between the thigh portion 20 and the calf portion 24. The angle A is very important because the patient's knee will therefore be immobilized in a flexed position. This position decreases any strain on the collateral and cruciate ligaments of the knee. In many prior devices, the knee is immobilized in a stretched position in which the ligaments are strained. This does not allow for proper healing. Thus, the angle A must be sufficient to produce knee ligament relaxation. After a careful analysis of medical data, the angle A has optimally been determined to be about 155°. It is satisfactory if the angle A is between about 145° and about 165°. A preferred range is between about 150° and about 160°.

Figure 4:
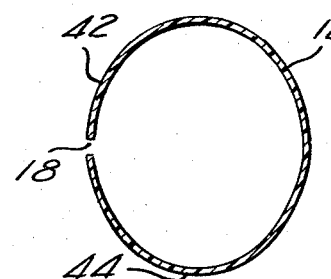
FIG. 4 is a sectional view taken through line 4—4 of FIG. 3.

Referring to FIGS. 3 and 4, an extreme upper portion 42 of the thigh portion 20 adjacent to the thigh opening 14 is essentially round in cross-section. Thus, the upper portion 42 is complimentarily shaped to fit around the patient's thigh.

Figure 5:
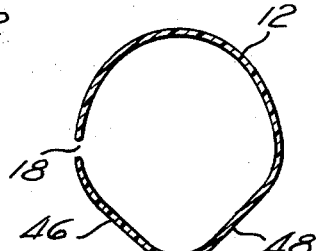
FIG. 5 is a sectional view taken through line 5—5 of FIG. 3.

Referring to FIGS. 4–7, a forward-most region 44 of the shell 12 is curved. However, as shown in FIGS. 3 and 5, on each side of the curved region 44, just above the knee portion 22, are located flat regions 46,48 which extend rearward. These flat regions 46,48 do not extend into the rear half of the shell 12 leaving the back side of the shell 12 curved.

Figure 6:
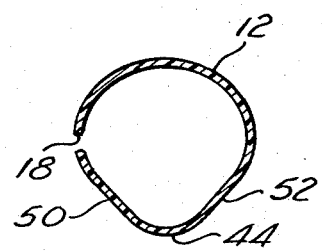
FIG. 6 is a sectional view taken through line 6—6 of FIG. 3.

Referring to FIGS. 2 and 6, located just below the knee portion 22 on either side of the curved front region 44, are flat areas 50,52 which extend rearward. The flat areas 50,52 do not extend into the rear of the shell 12 leaving the back side of the shell 12 curved.

Figure 7:
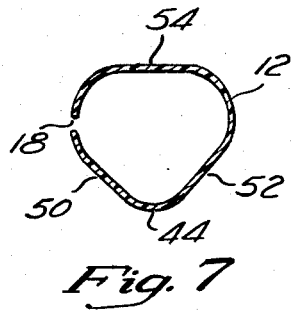
FIG. 7 is a sectional view taken through line 7—7 of FIG. 3.

Referring to FIGS. 2 and 7, the flat regions 50,52 extend downward on either side of the curved front 44 essentially to the calf opening 16. In addition, there is a flat region 54 located just above the calf opening 16 on the back side of the shell 12. Due to these flat regions 50, 52, 54, the cross-sectional configuration of the shell 12 just above the calf opening 16, as shown in FIG. 7, is triangular with rounded apexes.

The flat regions 46, 48, 50, 52, 54 are important because they seat flush against the patient's leg to prevent rotation of the patient's leg within the shell 12. As shown in FIGS. 5, 6 and 7, the flat regions 46, 48, 50, 52 and 54 are formed by indentations in the shell 12. These regions are also located so they will not unduly compress the leg so as to be harmful or uncomfortable. For example, the flat region 54 covers that portion of the patient's calf which has substantial fat and muscle tissue. With respect to FIG. 5, flat areas 46, 48 not only control rotation but also prevent the device 10 from sliding down relative to the knee.

To employ the device, all straps are disengaged from the buckles. The patient's leg is then inserted into the open end 14 of the thigh portion 20 and slid downward toward the calf portion 24. This sliding action will expand the opening 18 to permit the device 10 to be easily and comfortably slipped on. This expansion is made possible by the cooperative action of the opening 18 and the flexibility of the semi-rigid material. Thus, the material is rigid enough to immobilize the patient's knee, but pliable enough to permit the opening to expand allowing the device to be easily slipped on and off.

The leg continues to slide forward until the patient's knee is properly surrounded by the knee portion 22. The shell 12 is then tightened around the patient's thigh, knee and calf by threading the straps 26, 28, 30, 32 through their respective buckles 34, 36, 38, 40 and pulling them tight before effecting the lock. In this way, the opening 18 is narrowed so that the shell 12 substantially encompasses the circumference of the patient's leg. In this configuration, the shell 12 is essentially a tube of unitary construction which allows it to possess considerable structural strength. Thus, as a flat sheet, the semi-rigid material would be quite flexible. However, in the substantially closed tube configuration, shown in FIG. 1, the shell 12 has substantial strength. This allows the device 10 to provide secure and effective immobilization of the patient's knee and insures that the brace will remain in the flexed configuration defined by angle A.

I claim:

1. A device for immobilizing an individual's knee comprising:

an open-ended integral body formed into a substantially cylindrical tubular shell of semi-rigid material to provide substantial structural strength and secure immobilization, said shell having thigh, knee, and calf portions shaped to cover an individual's lower thigh, knee, and upper calf, respectively;

said body having a narrow longitudinal opening extending the length of said shell for permitting said shell to be slipped on and off the individual;

said tubular shell, at said thigh and calf portions including indentations which provide flat areas to prevent rotation of an individual's leg within the device; and said thigh portion extending at a sufficient angle from the calf portion to produce ligament relaxation of the individual's knee in a flexed position.

2. A device for immobilizing an individual's knee comprising:

an open-ended integral body formed into a substantially cylindrical shell of semi-rigid material, said body having thigh, knee, and calf portions sized to cover an individual's lower thigh, knee and upper calf, respectively;

means for reducing the circumference of said portions to tighten said shell of semi-rigid material contiguously around the individual's lower thigh, knee, and upper calf and effect immobilization; and said cylindrical shell, at said thigh and calf portions including indentations which provide flat areas which seat flush against the individual's leg above and below the knee to prevent any rotation of the leg when the shell is tightened.

3. The device of claim 1 wherein said angle is about 145° to about 165°.

4. The device of claim 3 wherein said angle is about 150° to about 160°.

5. A device for immobilizing an individual's knee comprising:

an open-ended integral body formed into a substantially cylindrical tubular shell of semi-rigid material, said shell having a knee portion which essentially surrounds the patient's knee to effect secure immobilization, said shell having indentations, located above and below said knee portion, for compressing the individual's leg and thereby preventing rotation of the individual's leg within the device.

6. A device for immobilizing an individual's knee comprising:
an open-ended integral body formed into a substantially cylindrical shell of semi-rigid material, said body having thigh, knee, and calf portions sized to cover an individual's lower thigh, knee, and upper calf, respectively; and
said calf portion including indentations which provide flat areas located on the back and sides of said body to apply pressure to said individual's calf and thereby prevent rotation of an individual's leg within said body.

* * * * *